United States Patent [19]

Gaylord, Jr.

[11] 3,990,440
[45] Nov. 9, 1976

[54] BODY PROTECTING METHOD
[75] Inventor: John F. Gaylord, Jr., Matthews, N.C.
[73] Assignee: Medical Specialties, Inc., Charlotte, N.C.
[22] Filed: June 16, 1975
[21] Appl. No.: 587,119

Related U.S. Application Data
[63] Continuation-in-part of Ser. No. 492,890, July 29, 1974, Pat. No. 3,937,218.

[52] U.S. Cl. .............................. 128/149; 128/165; 2/24
[51] Int. Cl.² ........................................ A61B 19/00
[58] Field of Search ........... 128/149, 165, 166, 153; 2/16, 22, 24, 239, 240

[56] References Cited
UNITED STATES PATENTS
| 2,550,461 | 4/1951 | Fick | 2/16 |
| 2,552,177 | 5/1951 | Hurt | 2/24 |
| 3,189,919 | 6/1965 | Chase | 2/16 |
| 3,266,058 | 8/1966 | Guttman | 2/239 |
| 3,322,118 | 5/1967 | Sotherlin | 128/149 |
| 3,648,291 | 3/1972 | Pankers | 128/165 X |
| 3,670,725 | 6/1972 | Gaylord, Jr. | 128/149 |

Primary Examiner—John D. Yasko
Attorney, Agent, or Firm—Bell, Seltzer, Park & Gibson

[57] ABSTRACT

An inexpensive, air permeable body protector adapted to be positioned on an elbow or heel of a bedridden patient for protecting against the development of decubitus ulcers or the like. The protector includes a resilient pad of porous foam material, the pad having a generally circular outline and a concave inner surface which defines an elbow or heel receiving pocket. A separate porous tubular knit sleeve is also provided which is adapted to be drawn onto and over the limb of the wearer and over the pad so as to surround the pad when positioned on the elbow or heel of the wearer.

8 Claims, 7 Drawing Figures

BODY PROTECTING METHOD

The present application is a continuation-in-part of copending application Ser. No. 492,890, filed July 29, 1974 and entitled DECUBITUS PAD, now U.S. Pat. No. 3,937,218.

The present invention relates to an inexpensive body protector, useful in preventing decubitus ulcers and the like, and which is adapted to be worn on an elbow, heel or like body portion of bedridden patients.

Various types and forms of protective pads have been proposed for use by patients, particularly elderly patients who are confined to bed for extended periods of time during an illness or convalescence. Such pads are designed to protect portions of the patient's body, such as the elbows and heels, from pressure and abrasive contact with the bed, which frequently contribute to the development of decubitus ulcers or bed sores. Such prior pads are usually specifically designed to be positioned to overlie one particular portion of the body, and they typically comprise a padded cushion member such as polyester fiber floss adhesively secured to a backing fabric. The cushion member is adapted to be folded, bent or seamed so as to be adapted to receive the intended body member therein. When the pad is intended for use on the heel, or the elbow, one or more straps are generally provided on the cushion member for extending across the arm or leg of the patient to maintain the padded cushion member in position.

Pads of the type described above, while serving to cushion the body member, have not been entirely satisfactory since they are undesirably bulky, they often have seams under the pressure point, they do not conform well to the arm or leg, and they are uncomfortable when worn for extended periods of time. Further, the straps employed for securing the pad to the elbow or heel often tend to restrict movement of the patient's arm or leg and impede blood circulation therein. This causes further discomfort, and also contributes to the development of decubitus ulcers. Still further, a few patients suffer an allergic reaction to the commonly employed pads of the polyester floss type, and such pads do not possess adequate porosity or breathability. Thus the pads have proven to be irritating to the skin of the wearer by holding moisture, such as perspiration and the like, against the skin.

Prior pads or protectors of the above-described type are also usually relatively expensive in view of the several manual operations required to manufacture the same, such as forming a pocket or gussett for the reception of the resilient pad, and then sewing the pad therein. Also, the materials employed in certain of the presently utilized pads may not be readily laundered and dried without risk of damage to the pad, thereby further adding to the overall cost of the protector.

It is accordingly an object of the present invention to provide a body protector which requires minimal manual manufacturing operations, and thus is sufficiently inexpensive to permit the same to be economically discarded after a single use, if desired.

It is another object of the present invention to provide a body protector which is characterized by a relatively smooth, soft, non-interrupted and non-irritating surface which directly contacts the skin of the wearer where pressure is normally applied.

It is a further object of the present invention to provide a body protector which may be applied to either an elbow or heel of a wearer, which is comfortable to wear for extended periods of time, and which is of a size sufficient to substantially fully surround and protect the bony prominences of the elbow or heel.

It is still another object of the present invention to provide a body protector of the described type which possesses sufficient porosity to permit ventilation of the underlying skin of the wearer, which is non-allergenic, and which may be repeatedly laundered without damage to the pad.

It is a more specific object of the present invention to provide a body protector which comprises a resilient pad formed of discrete particles of foam material to promote porosity, and which further includes a separate resilient knit fabric sleeve which is adapted to be drawn onto and over the limb of the wearer and thereby hold the pad in the desired position.

These and other objects and advantages of the present invention are achieved in the embodiment illustrated herein by the provision of a resilient pad of foam cushioning material which has a generally circular outline and a generally converging concavo-convex cross-sectional configuration, with the concave surface thereon defining an elbow or heel receiving pocket. The pad is formed from bonded discrete particles of a polymeric foam material to provide the desired porosity, and a porous tubular knit sleeve is adapted to be drawn onto and over the limb of the wearer and the pad so as to hold the pad in the desired position.

Some of the objects and advantages of the invention having been stated, others will appear as the description proceeds, when taken in connection with the accompanying drawings, in which.

Figure 5:
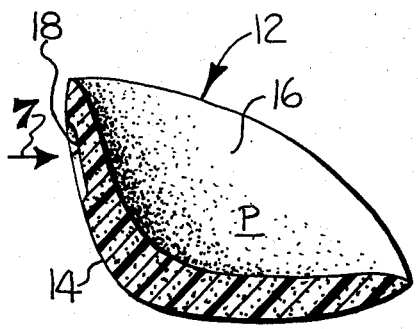
FIG. 5 is a sectional view of the foam pad taken substantially along the line 5—5 of FIG. 3.

Referring now specifically to the drawings, the illustrated body protector is indicated generally at 10 and comprises a resilient pad 12 of generally circular outline and having a substantially converging concavo-convex cross-sectional configuration, note FIG. 5. The pad 12 thereby defines a rear convex surface 14 and a forward or inner concave surface 16 which defines an elbow or heel receiving pocket P of considerable depth. Thus the thickness of the pad will be seen to be greater in the medial portion of the pocket where pressure is normally applied, while the peripheral edges are tapered and relatively thin to reduce the bulkiness thereof.

Figure 1:
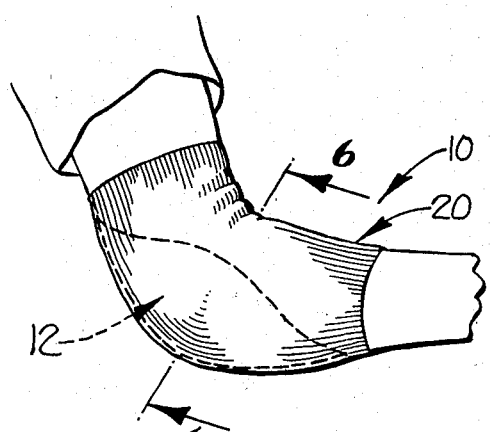
FIG. 1 is a fragmentary perspective view illustrating a body protector which embodies the present invention and which is positioned on the elbow of a wearer.
Figure 2:
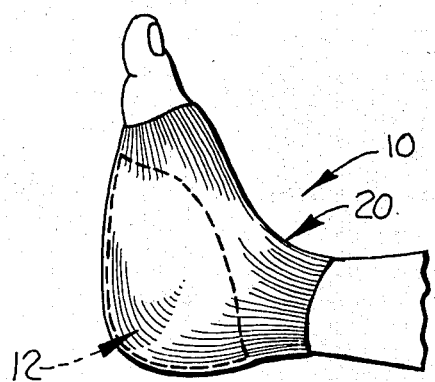
FIG. 2 is a fragmentary perspective view illustrating the body protector positioned on the heel of a wearer.
Figure 3:
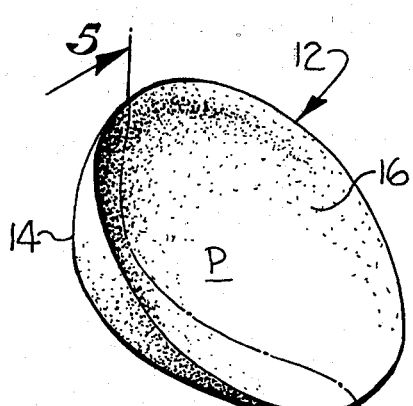
FIG. 3 is a perspective view of the foam pad incorporated in the body protector of the present invention.
Figure 4:
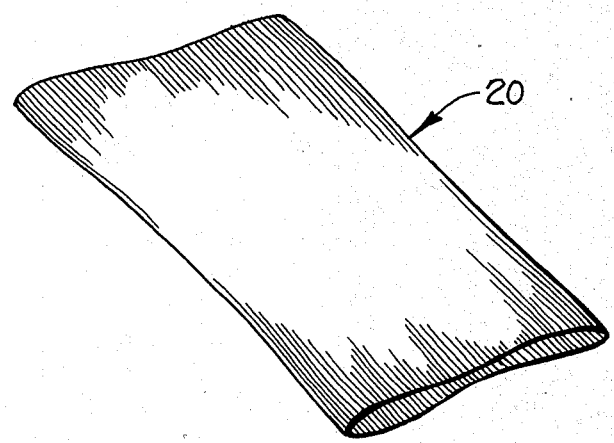
FIG. 4 is a perspective view of the tubular fabric sleeve of the present invention.

The pad 12 typically has an overall diameter of between about 6 and 8 inches for adult sizes, and so that it is adapted to substantially fully overlie the elbow or heel of the wearer, note FIGS. 1 and 2. Also, the depth of the pocket P will be seen to approximate one-half the overall diameter of the pad to further assist in protectively receiving the elbow or heel, as well as the adjacent surrounding areas. The thickness of the pad in the medial portion thereof is typically about one inch.

Viewing FIG. 5, it will be observed that the forward or horizontal portion of the pocket P has a somewhat greater longitudinal extent than does the rear or vertical portion. In order words, the center of curvature of the concave inner surface 16 and convex outer surface 14 is offset slightly toward the rear from the center of the circular outline of the pad. This configuration serves to improve the conformability of the pad to both the elbow and heel as hereinafter further explained. In addition, the rear convex surface 14 of the pad includes a slight indentation in the form of an arrow 18 on the rear or vertical portion, the arrow 18 serving to advise the wearer which way to install the pad as further explained below.

The pad 12 is preferably formed from adhesively bonded discrete particles of a polymeric foam material, since such material possesses a high degree of porosity which materially contributes to the comfort of the wearer. The foam material typically comprises polyurethane foam ground to fine crumbs, and the adhesive is preferably heat curable and typically comprises long polymer polyether urethane in a chlorinated solvent, and mixed in a 1:5 ratio by weight with the foam.

The pad may conveniently be fabricated by a vacuum molding process which employs a cooperating pair of concave and convex perforated mold surfaces. In such case, a predetermined amount of the dry, particulate foam material having the heat curable adhesive mixed therewith, is deposited upon the concave mold surface and held thereon by a vacuum acting through the perforations in the surface. The mating convex mold surface is then brought into face-to-face relationship with the concave mold surface, and the material is then heated by steam or the like to cure the adhesive. The mold surfaces may then be separated and the resulting pad 12 is completely formed, with the arrow 18 being formed by a corresponding projection on the concave mold surface. Further details of a suitable process and apparatus for fabricating the pad 12 may be obtained from the copending application of Herman S. Johns, Ser. No. 563,585, filed Mar. 31, 1975, and having a common assignee with the present application.

The overall density of the resulting pad 12 is typically about 3 to 4 pounds per cubic foot, and in this regard, the density in various portions of the molded product may be varied by suitably depositing and shaping the particulate foam material on the concave mold surface as described above. For example, the central or medial portion of the pad may have a relatively low density of about 2½ pounds per cubic foot to promote softness, while the peripheral edge may have a somewhat higher density of about 3½ to 4 pounds per cubic foot to provide sufficient integrity about the relatively thin peripheral edge.

The body protector 10 further comprises a separate tubular fabric sleeve 20 having a longitudinal length somewhat greater than the diameter of the pad, and which is adapted to be drawn onto and over the limb of the wearer, and onto and over the pad 12 as seen in FIGS. 1 and 2 so as to surround and completely cover the pad when positioned on the elbow or heel of the wearer. The sleeve 20 is preferably constructed from a single layer of air permeable fabric material to thereby make the sleeve as lightweight as possible and further contribute to its overall porosity. Also, the sleeve preferably comprises a readily stretchable knit construction to permit a high degree of radial stretchability while not binding the limb of the wearer. Further, the sleeve is desirably fabricated from polymeric and hydrophobic yarns, such as nylon, since such materials permit moisture and perspiration to be readily conducted through the fabric and away from the wearer and thus facilitate maintaining the skin free from irritation. Such polymeric yarns are also desirable in that the resulting fabric has a low coefficient of friction, and the pad thus slides easily on the sheet of the bed.

As seen in FIG. 1, the protective pad 10 is positioned on the arm of the wearer. In this regard, the pad 12 is initially positioned such that the pocket P receives the elbow, with the elongated forward portion of the pad being positioned to underlie the forearm of the wearer for maximum conformability. In this regard, the arrow 18 serves to readily identify to the wearer the rear portion of the pad which is intended to be positioned to the rear of the elbow, thereby facilitating and ensuring its proper application. As will be apparent, the concave surface 16 is smoothly curved, without irregularities or seams, and thereby provides a soft, nonirritating surface throughout the full area thereof. Also, the fact that the peripheral edge of the pad overlies a substantial area surrounding the elbow serves to ensure full protection for all areas of the skin which may rest upon or contact the bed.

Figure 6:
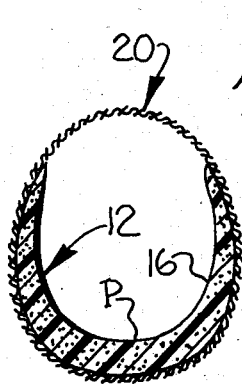
FIG. 6 is a sectional view of the foam pad taken substantially along the line 6—6 of FIG. 1.
Figure 7:
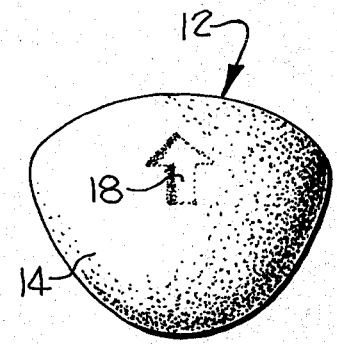
FIG. 7 is a rear elevation view illustrating the rear surface of the pad and looking in the direction of the arrow 7 in FIG. 5.

With the pad 12 held against the elbow in the above position, the tubular sleeve 20 is drawn onto and over the arm, and onto and over the pad so as to substantially fully overlie and cover the convex surface 14 of the pad. The stretchability of the sleeve facilitates its positioning over the arm and pad, and serves to resiliently hold and maintain the pad in its desired position, while only lightly contacting the arm. Thus no significant binding forces are applied to the arm by the sleeve. Viewing FIG. 6, it will also be observed that the pad 12 possesses sufficient flexibility such that the sleeve 20 is able to readily conform the pad to the circumferential outline of the arm of the wearer.

The pad 12 and sleeve 20 may be similarly applied to the heel of a wearer as seen in FIG. 2. In this case, the rear portion of the pad should be oriented to underlie the rear portion of the heel for maximum conformability, and the arrow 18 again serves to readily identify the rear portion to the wearer so that the pad is properly applied.

In the drawings and specification, there has been set forth a preferred embodiment of the invention, and although specific terms are employed, they are used in a generic and descriptive sense only and not for purposes of limitation.

That which is claimed is:

1. A method for protecting a limb of a bedridden patient or the like, and characterized by a relatively smooth, soft, non-irritating surface in contact with the body of the patient where pressure is normally applied, and comprising the steps of positioning a pad of bonded discrete particles of resilient foam material on a limb of the wearer at the elbow or heel, the pad having a generally converging concavo-convex cross-sectional configuration and a generally circular peripheral edge such that the concave inner surface thereof defines a smoothly curved, non-interrupted pocket of considerable depth approximating one-half the overall diameter of the pad and receiving the elbow or heel of the wearer so as to protect the elbow or heel and adjacent surrounding areas, and positioning a porous tubular sleeve in surrounding relation over the pad and limb of the wearer, the sleeve being free of any interconnection with the pad and being resiliently stretchable in the radial direction to facilitate positioning the sleeve over the pad and limb of the wearer and to snugly hold the pad in a desired position on the limb of the wearer.

2. The method as defined in claim 1 wherein the pad has an overall diameter of between about six to eight inches so as to substantially fully overlie the elbow or heel of the wearer.

3. The method as defined in claim 2 wherein the sleeve comprises a knit fabric having a length somewhat greater than the diameter of the pad so as to completely cover the pad while holding the same in position on the limb.

4. The method as defined in claim 3 wherein the sleeve comprises a knit fabric of polymeric yarns to facilitate the passage of moisture and perspiration therethrough and thereby further contribute to the comfort of the wearer.

5. The method as defined in claim 1 wherein the pad has a density of between about three to four pounds per cubic foot.

6. The method as defined in claim 1 wherein the pad further comprises a forward portion of somewhat greater longitudinal extent than the rear portion thereof, and the pad further comprises indicia means carried on the pad for readily distinguishing the forward and rear portions to thereby facilitate the proper application of the pad on either the elbow or heel by the wearer.

7. The method as defined in claim 6 wherein the indicia means comprises an indentation in the surface of the pad.

8. The method as defined in claim 1 wherein the pad has a relatively low density of about two and one-half pounds per cubic foot in the medial portion thereof to promote softness, and a relatively high density of about three and one-half to four pounds per cubic foot about the peripheral edge to provide sufficient integrity thereto.

* * * * *